(12) United States Patent
Barral

(10) Patent No.: US 10,203,491 B2
(45) Date of Patent: Feb. 12, 2019

(54) PATHOLOGY DATA CAPTURE

(71) Applicant: Verily Life Sciences LLC, Mountain View, CA (US)

(72) Inventor: Joëlle K. Barral, Mountain View, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 55 days.

(21) Appl. No.: 15/225,247

(22) Filed: Aug. 1, 2016

(65) Prior Publication Data

US 2018/0031817 A1    Feb. 1, 2018

(51) Int. Cl.
G02B 21/36 (2006.01)
G02B 21/02 (2006.01)
G02B 27/00 (2006.01)
G06F 19/00 (2018.01)
G16H 10/40 (2018.01)

(52) U.S. Cl.
CPC ......... *G02B 21/365* (2013.01); *G02B 21/025* (2013.01); *G02B 27/0093* (2013.01); *G06F 19/321* (2013.01); *G16H 10/40* (2018.01)

(58) Field of Classification Search
None
See application file for complete search history.

(56) References Cited

U.S. PATENT DOCUMENTS 6,005,964 A    12/1999 Reid et al.
6,441,958 B1   8/2002 Yeung et al.
8,199,358 B2   6/2012 Eichhorn et al.
8,350,905 B2   1/2013 Yamada
8,600,143 B1   12/2013 Kulkarni et al.
(Continued)

FOREIGN PATENT DOCUMENTS

DE  10 2012 005 126 A1   9/2013
WO  WO 2005/121863 A1   12/2005
(Continued)

OTHER PUBLICATIONS

International Search Report and Written Opinion dated Nov. 8, 2017, from the International Searching Authority, for International Application No. PCT/US2017/044541, filed Jul. 28, 2017, 14 pages.

*Primary Examiner* — Frederick D Bailey
(74) *Attorney, Agent, or Firm* — Christensen O'Connor Johnson Kindness PLLC

(57) ABSTRACT

A method for pathology data capture includes magnifying a pathology sample with a microscope to form magnified pathology images. The method also includes recording the magnified pathology images with a digital camera optically coupled to the microscope, and recording voice annotations from a user of the microscope with a microphone. The magnified pathology images and the voice annotations are transferred to a processing apparatus electrically coupled to the digital camera and the microphone. The processing apparatus performs operations including recording the magnified pathology images and the voice annotations to a storage medium, indexing the magnified pathology images and the voice annotations with respect to recording time, and tagging the voice annotations of the user to one or more specific locations in the magnified pathology images.

20 Claims, 4 Drawing Sheets

(56) References Cited

U.S. PATENT DOCUMENTS

| | | | |
|---|---|---|---|
| 2005/0051614 A1* | 3/2005 | Albany | G02B 21/34 235/375 |
| 2005/0123181 A1* | 6/2005 | Freund | G02B 21/365 382/128 |
| 2007/0122145 A1* | 5/2007 | Chang | G02B 13/009 396/529 |
| 2011/0122242 A1 | 5/2011 | Garud et al. | |
| 2012/0044343 A1* | 2/2012 | Kurihara | G01B 11/028 348/86 |
| 2012/0314949 A1* | 12/2012 | Grady | G06T 7/11 382/173 |
| 2013/0342674 A1 | 12/2013 | Dixon | |
| 2015/0130920 A1 | 5/2015 | Zou et al. | |
| 2016/0033753 A1* | 2/2016 | Saito | G02B 21/367 348/79 |
| 2016/0070945 A1* | 3/2016 | Merlo | G02B 21/248 235/375 |
| 2016/0180060 A1* | 6/2016 | Nelson | A01G 22/00 702/19 |
| 2017/0300622 A1* | 10/2017 | Laviolette | G06F 19/321 |
| 2018/0031817 A1* | 2/2018 | Barral | G02B 21/365 |

FOREIGN PATENT DOCUMENTS

| | | | |
|---|---|---|---|
| WO | WO2007039373 | * | 3/2007 |
| WO | 2015/114485 A1 | | 8/2015 |

* cited by examiner

| Image Frame | Rec. Time (μSec) | Trascribed Text | Stage Pos. (X,Y[μm]) | Mag. | Gaze (Quadrant) |
|---|---|---|---|---|---|
| 1 | 1–3 | This | 10, 30 | 20x | 1 |
| 2 | 4–7 | looks | 12, 30 | 20x | 1 |
| 3 | 8–11 | like | 12, 30 | 20x | 1 |
| 4 | 12–15 | lim- | 12, 32 | 20x | 1 |
| 5 | 16–19 | phatic | 22, 42 | 20x | 2 |
| 6 | 20–23 | tissue | 77, 43 | 20x | 2 |
| 7 | 24–27 | and | 105, 43 | 20x | 2 |
| 8 | 28–31 | may be | 130, 46 | 40x | 3 |
| 9 | 32–35 | ... | 130, 46 | 40x | 3 |
| 10 | 36–39 | benign | 136, 47 | 40x | 4 |
| ...N | 40–N | ... | X, Y | 0–2000X | 1–4 |

PATHOLOGY DATA CAPTURE

TECHNICAL FIELD

This disclosure relates generally to systems/methods for aiding in pathology.

BACKGROUND INFORMATION

Pathology is a medical discipline related to the study and diagnosis of disease. Most frequently pathology involves the analysis and examination of body-fluid, tissue, and cell samples. As a field of general study and research, pathology relates to four aspects of disease: (1) etiology, (2) pathogenesis, (3) morphologic changes, and (4) consequence of morphologic changes.

The field of pathology dates back to antiquity. Many early societies possessed a rudimentary understanding of biological conditions as a result of dissection/examination. By the Hellenic period of Greece, a causal study of disease had emerged in human culture. Human understanding of disease through pathology continued to advance piecemeal as time progressed; for instance many advances in pathology are attributable to the medieval era of Islam.

However, modern pathology only emerged as a distinct field of study in the late 1800's with the advent of microbiology. Now pathology is a major medical practice that is divided into a number of subdisciplines. In all of these subdiciplines, collaboration between multiple doctors may be important to ensure accurate diagnosis. Furthermore, training pathologists requires the trainee to examine a huge number of samples in order for the trainee to become familiar with the many possible variants of disease.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for pathology data capture are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The instant disclosure improves pathology data capture by cheaply integrating slide digitization into the pathologist's workflow (non-disruptively). In modern pathology, sometimes pathology samples are scanned at high-resolution to create a digital database. Depending on the complexity of the scan this may take a long time and result in a huge amount of data being collected. Furthermore large portions of the sample may be irrelevant to diagnosis or training (e.g., if a sample is several centimeters large and the diseased cells are only in a 1 mm area, digitizing the whole sample is a waste of memory). Accordingly, by only recording the magnified images/video that a trained pathologist chooses to examine, in conjunction with the pathologists vocal annotations, a database that only contains information germane to the diagnosis/identification of disease is created.

Figure 1:
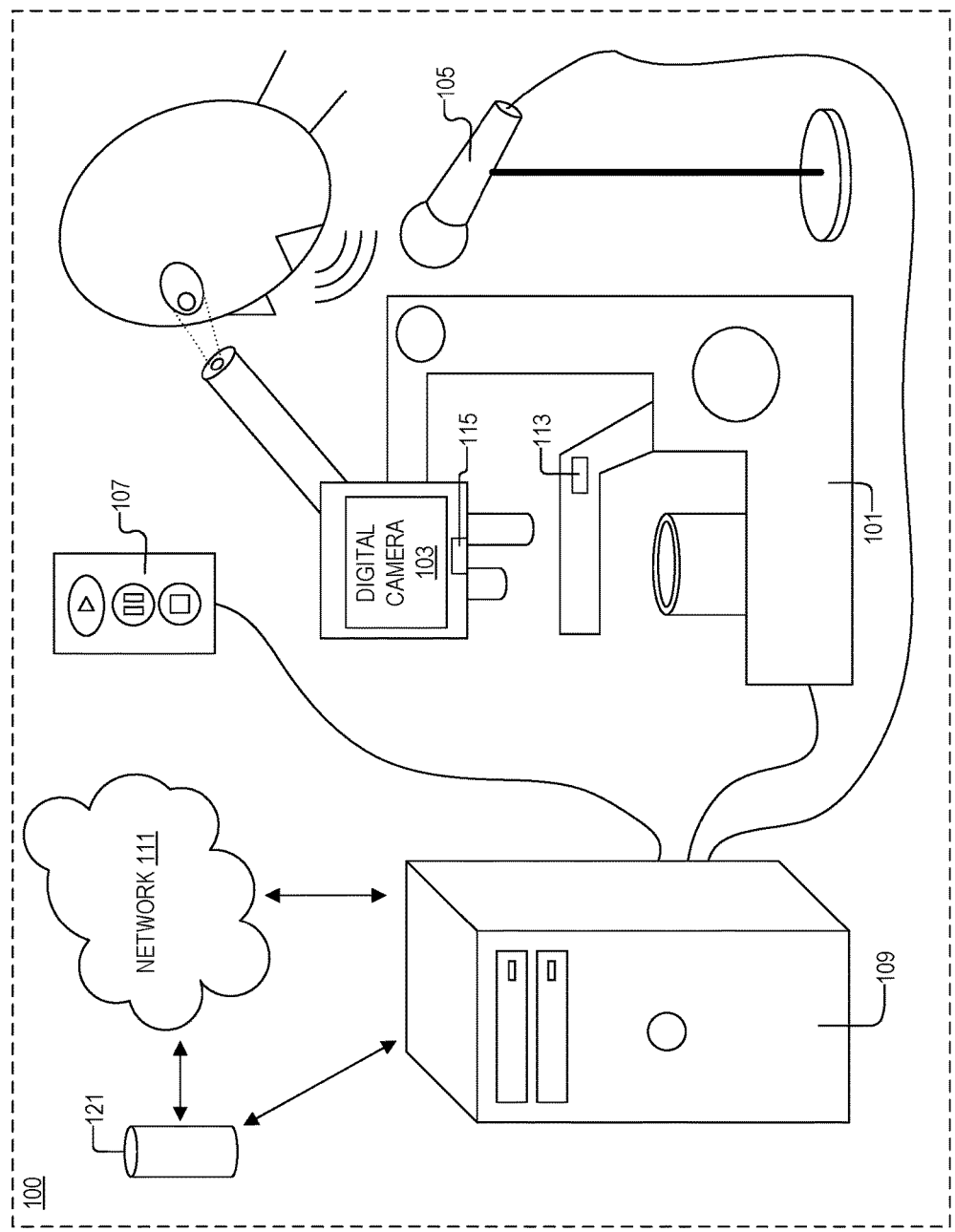
FIG. 1 illustrates a system for pathology data capture, in accordance with an embodiment of the disclosure.

FIG. 1 illustrates a system 100 for pathology data capture, in accordance with an embodiment of the disclosure. System 100 includes: microscope 101, digital camera 103, microphone 105, controller 107, processing apparatus 109, network 111, and storage 121. System 100 provides for the continuous recording of what the pathologist sees, performs automatic mosaicking of the resulting high-resolution images, captures slide displacement, and annotates the reconstructed mosaicked image with diagnostic information provided by the pathologist.

Microscope 101 houses digital camera 103, and digital camera 103 is optically coupled to microscope 101 to continuously capture magnified pathology images produced by microscope 101. In some embodiments, digital camera 103 may not be housed in microscope 101 and may be an add-on. However, one skilled in the art will appreciate that digital camera 103 may be coupled to microscope 101 in a number of ways, in accordance with the teachings of the present disclosure. It is worth noting that microscope 101 has many different magnification settings, all of which can be recorded by digital camera 103. Additionally, microphone 105 is coupled to receive voice annotation of a user/pathologist.

Processing apparatus 109 (i.e., a desktop computer) is electrically coupled to digital camera 103 to receive the magnified pathology images and electrically coupled to microphone 105 to receive the voice annotation from the pathologist (i.e., the cartoon person). It is worth noting that all devices in system 100 may communicate wirelessly in some embodiments. Processing apparatus 109 includes logic that when executed by processing apparatus 109 causes processing apparatus 109 to perform operations including: recording the magnified pathology images and the voice annotation to a storage medium (e.g., hard drive, RAM, ROM, flash memory, etc.), and indexing the magnified pathology images and the voice annotation with respect to recording time. Although a desktop computer is depicted as processing apparatus 109, other computing devices can be used as processing apparatus 109. For example tablets, phones, laptops, remote servers, processors/microcontrollers incorporated in microscope 101, etc. can all function as processing apparatus 109.

In the depicted embodiment, the magnified pathology images and the voice annotation form a database, and the database may be uploaded to remote or local servers via network 111. As shown processing apparatus 109 may be both electrically coupled to network 111 and storage 121. In other embodiments, processing apparatus 109 may also exist on remote servers in the cloud, or processing apparatus 109 may be distributed across many devices/systems. However, as depicted, processing apparatus 109 may also exist locally.

Microscope 101 has a stage including first mechanical to electrical transducers 113 to track a position of the stage. The position of the stage may be sent from the first mechanical to electrical transducers 113 to the processing apparatus 109. Similarly, second mechanical to electrical transducers 115 are coupled to microscope 101 to measure the magnification setting of microscope 101. The magnification setting may be sent from the second mechanical to electrical transducers 115 to processing apparatus 109. However, in another or the same embodiment, the magnification setting may be captured through an external video camera.

As illustrated controller 107 is coupled to processing apparatus 109. Controller 107 may be used to control image/video capture of digital camera 103, record voice annotations from microphone 105, adjust the position of the microscope stage, and adjust illumination settings of microscope 101 (e.g., make illuminator brighter/darker, polarized, top-illuminated, bottom-illuminated, etc.). Although in the depicted embodiment controller 107 is wired to processing apparatus 109, in other embodiments controller 107 may communicate with processing apparatus 109 wirelessly. In some embodiments, controller 107 may be a virtual controller running on processing apparatus 109, and may receive vocal instructions through microphone 105, or a kinetic instructions via a mouse/keyboard connected to the processing apparatus 109. In one embodiment the user may state commands to microphone 105, and a virtual/embedded controller in processing apparatus 109 executes the instructions. For example, the user may say "OK microscope, turn on microscope lighting and start visual and audio recording", "pause audio recording", "pause visual recording", "move the microscope stage one frame to the left", "change to linearly polarized light", etc. In these and other embodiments, microphone 105 can be integrated into digital camera 103 and/or microscope 101, or it can be a separate device. Microphone 105 can start recording synchronously with digital camera 103 or it can be manually or automatically turned on when digital camera 103 is on. Alternatively, microphone 105 can passively listen for keywords before starting recording (e.g., "OK Microscope").

Digital camera 103 can be either continuously on or it can be turned on by the pathologist when a new slide is examined. Digital camera 103 can also be motion triggered (i.e., it starts recording when the slide starts moving and/or the zoom or focus level of microscope 101 is changed). Alternatively, a presence sensor (optical or otherwise) can be added to the eyepiece of microscope 101, and digital camera 103 is automatically turned on when the presence of the pathologist looking through microscope 101 is detected.

Microscope 101 may come with, or be outfitted to include, gaze detection hardware and software (depicted as the two dashed lines from the eyepiece of microscope 101 to the user's eyes). Accordingly, system 100 may track the gaze of the user to determine a region of interest (e.g., cancer cells in an image); the region of interest may be indexed with respect to recording time, magnification setting, and magnified pathology image. For example, the time a pathologist is looking at a region can be used as a proxy for confidence and/or an indication that the region is of more interest.

In one embodiment, digital camera 103 outputs a video including the magnified pathology images, and processing apparatus 109 further includes logic that causes processing apparatus 109 to stitch together frames in the video to form a plurality of high-resolution images. This can be used to create comprehensive magnified pathology images of only the relevant portions of a sample at various levels of magnification (see infra FIG. 3). Moreover, forming the image database does not interrupt the pathologists workflow since, in this embodiment, only the portions of the sample the pathologist looks at are used to stitch together the high-resolution images. Videos and vocal annotations may be recorded simultaneously, or they can be time-stamped and recorded separately, to be combined later.

Figure 2:
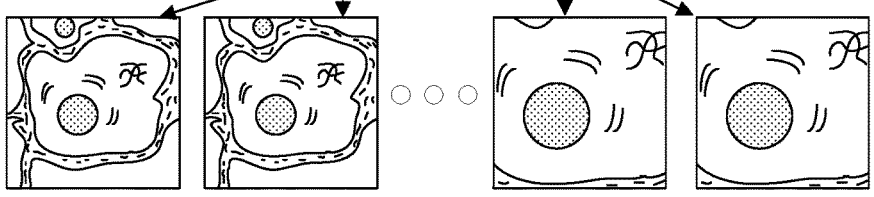
FIG. 2 illustrates a pathology database, in accordance with an embodiment of the disclosure.

FIG. 2 illustrates a pathology database 201, in accordance with an embodiment of the disclosure. Pathology database 201 may be created using system 100 of FIG. 1, and may be stored on storage 121 (e.g., hard drives, solid state drives, etc.). As shown in the depicted embodiment, pathology database 201 includes pathology images (e.g., video frames) that were captured by a digital camera (e.g., digital camera 103). The pathology images are indexed with respect to their frame number, recording time, the voice annotation of the pathologist (transcribed), microscope stage position, magnification they were collected at, and location of pathologist gaze. One skilled in the art will appreciate that the system depicted in FIG. 1 can be used to create a database with any number of dimensions and inputs and is not restricted to those dimensions/inputs depicted here.

As illustrated a digital camera (e.g., digital camera 103) optically coupled to a microscope (e.g., microscope 101) may start recording images of pathology samples as a digital video or still frames. Each frame of the video is indexed with respect to its capture time. For example in the depicted embodiment, frame one was captured during the first three microseconds of recording, frame two was captured in the fourth through seventh microseconds of recording, etc. A microphone (e.g., microphone 105) may also record the voice annotation of a user of the microscope. The vocal annotations may be converted into text and/or indexed to their respective recording time and video frame. In the depicted embodiment, while frame one was captured (during the first three microseconds of recording) the pathologist said the word "this"; in subsequent frames the pathologist stated "looks like lymphatic tissue and may be benign." In one embodiment, other metadata about the patient along with geographical information (which might later unveil an outbreak of a virus in a specific geographic area for example) may also be collected and included in the pathology database.

The system may also record the position of the microscope stage and index it with respect to the recording time and the magnified pathology images. In the depicted embodiment, the location of the stage is measured with X, Y coordinates from a (0,0) point which is the lower left hand position of the stage, and the stage movement is measured in microns. However, in other embodiments the stage axis may be oriented differently (e.g., the (0,0) point is located at the bottom right hand position of the stage), the units of measurement may be different (e.g., mm, cm, etc.), and the Z position of the stage may also be recorded. Furthermore, "stage position" should be broadly construed because it is used to identify specific locations on samples, which one skilled in the art will appreciate may be achieved in any number of ways. In one embodiment, stage position is determined optically with respect to the dimensions of the slide being imaged, and not with respect to the microscope hardware. As shown, the magnification that a specific frame was viewed with is also recorded with respect to recording time, transcribed text, stage position, and gaze quadrant.

The user's gaze may also be indexed with respect to the other dimensions/inputs illustrated and discussed. In the depicted embodiment, the gaze of the user/pathologist is measured in quadrants; meaning the image the user sees is subdivided into four sub-images, and the system records which sub-image the user was looking at during the recording time. This may be achieved with hardware/software installed in the microscope, or other external systems, as one skilled in the art will appreciate that there are many different ways to detect gaze. Moreover, while the embodiment depicted here only illustrates very generally where the pathologist/microscope user was looking, in other embodiments the exact coordinates that the user was looking at are recorded.

In one embodiment, indexing the magnified pathology images and the voice annotation may include tagging the voice annotation of the user to a region of interest in the magnified pathology images. For instance, in the embodiment depicted above, the pathologist's diagnosis of "benign" is associated with stage position coordinates (136, 47) at 40× magnification, and he/she was looking in quadrants 3 and 4. This allows a person reviewing the pathologist's work to know exactly where the pathologist was looking when the determination of "benign" was made. Further the person reviewing the pathologist's work knows the history of examination (how much of the slide had been examined up to that point). In the depicted embodiment, the processing apparatus may further include logic that when executed by the processing apparatus causes the processing apparatus to convert the pathologist's voice annotation to text, and the text is indexed with respect to recording time and the magnified pathology images, among the other dimensions/inputs mentioned and discussed. In another or the same embodiment, the pathologist may be able to review the pathology images collected and directly annotate the image to show a region of interest (e.g., circle the cancer cells on the digital image, place a star next to an unknown cell formation, etc.).

Lastly, it is worth noting that more than one pathologist may look at and annotate a pathology sample. Additional database rows and/or columns may be added so that information from both pathologists is captured. Both of the pathologists' input can then be compared to generate a ground truth/augment regarding what is known about the sample/slide. Redundancy of information about a pathology sample may make the diagnosis in the pathology database more robust.

Figure 3:
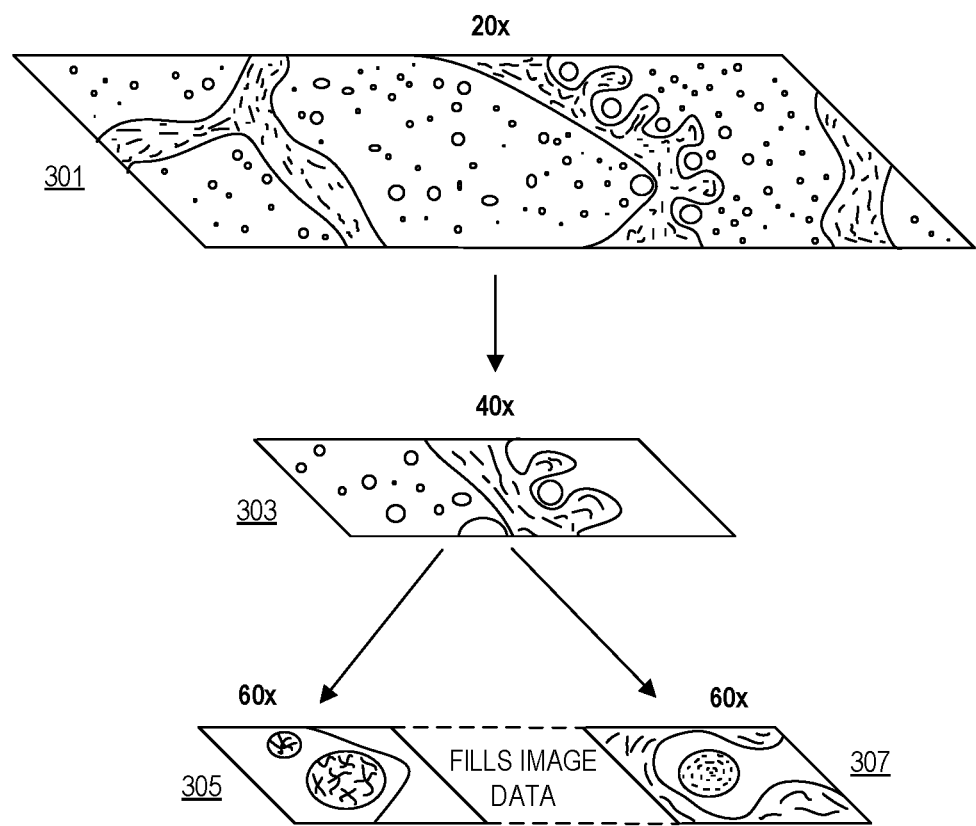
FIG. 3 illustrates image entries in the pathology database of FIG. 2, in accordance with an embodiment of the disclosure.

FIG. 3 illustrates image entries in the pathology database of FIG. 2, in accordance with an embodiment of the disclosure. In the depicted embodiment, several magnifications of the same pathology sample are shown. In this embodiment, a pathologist used an imaging system (e.g., system 100 of FIG. 1) to look at several portions of a pathology sample under different levels of magnification. It is important to note that the pathologist did not look at the whole sample under all magnifications. For instance under 20× the whole sample may be visible; however, because only a small portion of the sample is relevant for making a diagnosis, the pathologist only bothered to zoom in on the one portion of the sample. Accordingly, the pathologist zoomed in to view that portion under 40× magnification. The pathologist then further zoomed in on two separate spots contained in the 40× portion of the image, and viewed these under 60× magnification. It is possible that these small sections of the pathology sample are the only portions germane to diagnosis. Since a camera was capturing all of the action by the pathologist, the camera has captured incomplete pictures of the sample under 40× and 60× magnification. However, this does not impact the ability of someone reviewing the pathologist's work to understand why the diagnosis was made, since the person reviewing the work can see the portions of the sample relevant to diagnosis (and hear a recording, or view transcribed text, of the pathologist's vocal annotations).

Further in one embodiment, to make the holes in the different levels of magnification more visually appealing, the processing apparatus may generate image data for the un-imaged holes. This allows a reviewer of the captured images to fluidly move between the imaged portions of the sample without visual discontinuity from the un-imaged portions. In this embodiment, the generated image data may be clearly identified as not actual image data (e.g., the generated image data may be outlined with red lines, appear in grayscale, appear partially transparent, or contain overlaid words like "generated data", etc.). In one embodiment, a machine learning algorithm is used to generate the image data.

Figure 4:
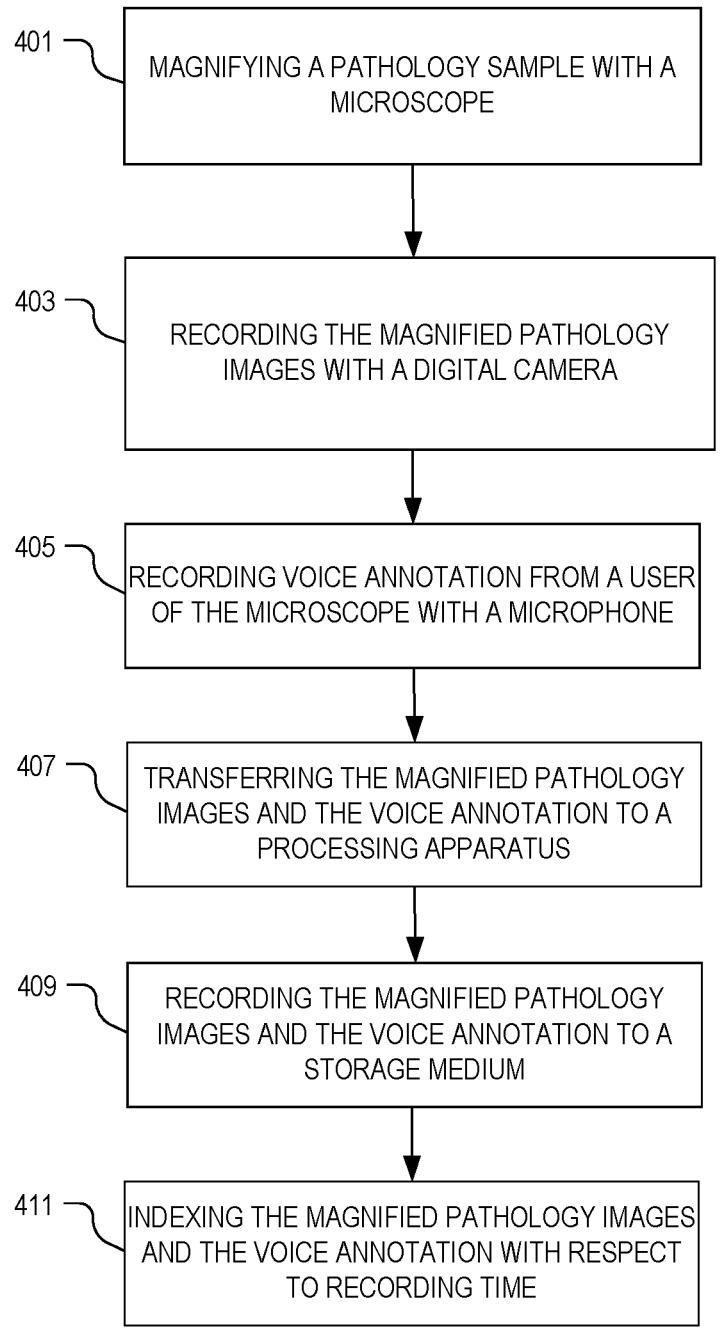
FIG. 4 is a flow chart illustrating a method of pathology data capture, in accordance with several embodiments of the disclosure.

FIG. 4 is a flow chart illustrating a method 400 of pathology data capture, in accordance with several embodiments of the disclosure. The order in which some or all of process blocks 401-411 appear in method 400 should not be deemed limiting. Rather, one of ordinary skill in the art having the benefit of the present disclosure will understand that some of method 400 may be executed in a variety of orders not illustrated, or even in parallel.

Block 401 illustrates magnifying a pathology sample with a microscope to form magnified pathology images. As discussed above, a pathologist may examine pathology samples through a conventional microscope, or may look at pathology samples with a custom microscope that is specially adapted to the systems described here (e.g., system 100 of FIG. 1 with all depicted components embedded in microscope 101).

Block 403 shows recording the magnified pathology images with a digital camera optically coupled to the microscope. The microscope discussed may include a digital camera that is constantly recording video or still frames of the portions of the sample that the pathologist is viewing. In one embodiment, the processing apparatus stitches together frames in the video to form a plurality of high-resolution images (see supra FIG. 2)

Block 405 depicts recording voice annotation from a user of the microscope with a microphone. While the pathologist is viewing the magnified pathology images, the pathologist may be simultaneously vocally annotating what he/she sees. For example the pathologist may look at particular portion of the magnified pathology image and state his/her general impression about the image. For example the pathologist may say something to the effect of "while the cells in this portion of the sample are a little atypical, there doesn't seem to be any melanoma" and the microphone may record this speech. However, sometimes recording voice annotation may be asynchronous: the pathologist doesn't comment while viewing, but when done examining the slide, he/she dictates the whole report.

Block 407 shows transferring the magnified pathology images and the voice annotation to a processing apparatus electrically coupled to the digital camera and the microphone. Transferring the magnified pathology images and the voice annotation may occur in real time (i.e., as the microphone and the camera are capturing image data and sound data) or may occur after the pathologist finishes the whole recording. One skilled in the art will appreciate that there are many different ways to facilitate transfer of both images and sound data, and that any one of these techniques may be used in accordance with the teachings of the present disclosure.

Block 409 illustrates using the processing apparatus to performs operations including recording the magnified pathology images and the voice annotation to a storage medium. The storage medium may be RAM, ROM, flash memory, hard disk, or the like. The processing apparatus may store the information locally (e.g., on a hard drive contained in, or wired/wirelessly connected to, the processing apparatus) or may upload this information to a remote sever, distinct from the processing apparatus, via the internet or local area network. In one embodiment, the processing apparatus forms a database with both the magnified pathology images and the voice annotation. Further, the processing apparatus may convert the speech to text using any natural language processing technique; the text may be indexed with respect to the recording time and the magnified pathology images.

Block 411 depicts using the processing apparatus to performs operations including indexing the magnified pathology images and the voice annotation with respect to recording time. In one embodiment, indexing the magnified pathology images and the voice annotation includes tagging the voice annotation of the user to a specific location in the magnified pathology images. Thus anyone reviewing the pathologist's work can clearly see/hear the rationale behind the diagnosis.

In one embodiment, the position of the microscope stage is recorded to provide information about the location of where the pathologist was looking. Again, this may be useful to determine why a pathologist made a particular diagnosis. Stage position may be determined optically with a scale bar on the sample or the like. Magnification level may also provide useful position information. The magnification level of the microscope may be transferred to the processing apparatus, and the processing apparatus indexes the magnification level with respect to the recording time, the magnified pathology images, and the position of the microscope stage. This optical information may be used independently from, or in conjunction with, the physical position of the microscope stage to determine the location of an image relative to the pathology sample.

In one embodiment, the motion data of the stage could be used to inform the camera to turn on. For example, when the stage is stationary the camera will not capture videos, but will capture images (single frames). Conversely, when the stage is moving the camera may collect video. The X, Y, and Z vectors of movement may be treated separately (for example, video would be captured when the stage is moving in the X, Y directions, but not when the stage is moving in the Z direction).

In one embodiment, the processing apparatus may be configured to remove image artifacts from the magnified pathology images. If the motion of the stage (X, Y, Z) has been recorded, the computed motion can be compared to the recorded motion, and the difference can be used to assess the quality of the video data: if both are in agreement, the video data is highly reliable. But in the case of a strong discrepancy, the video data contains artifacts, and the corresponding frames can be tagged and not used for further processing, mosaicking, etc.

In one embodiment the processing apparatus further tracks the gaze of the user to determine a region of interest, and the region of interest is indexed with respect to recording time, the magnification setting, and magnified pathology images. This allows someone reviewing the work of the pathologist to clearly identify the important portions of the magnified pathology images.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for pathology data capture, comprising:
    magnifying a pathology sample with a microscope to form magnified pathology images;
    recording the magnified pathology images with a digital camera optically coupled to the microscope, wherein the magnified pathology images are included in a video;
    recording voice annotations from a user of the microscope using a microphone;
    transferring the magnified pathology images and the voice annotations to a processing apparatus electrically coupled to the digital camera and the microphone, wherein the processing apparatus performs operations including:
    recording the magnified pathology images and the voice annotations to a storage medium;
    indexing the magnified pathology images and the voice annotations with respect to recording time and tagging the voice annotations of the user to one or more specific locations in the magnified pathology images;
    stitching together the magnified pathology images in the video to form a plurality of high-resolution images, wherein the plurality of high-resolution images include un-imaged holes; and generating image data that is not actual image data for the un-imaged holes using a machine learning algorithm, wherein the un-imaged holes are disposed between individual magnified pathology images used to form the plurality of high-resolution images.

2. The method of claim 1, wherein the processing apparatus further tracks the gaze of the user to determine a region of interest, and wherein the region of interest is indexed with respect to recording time, the magnified pathology images, and wherein the one or more specific locations includes the region of interest.

3. The method of claim 1, further comprising converting the voice annotations to text using the processing apparatus, wherein the text is indexed with respect to the recording time and the magnified pathology images.

4. The method of claim 1, further comprising recording a position of a microscope stage and transferring the position of the microscope stage to the processing apparatus, wherein the position of the microscope stage is indexed with respect to the recording time and the magnified pathology images.

5. The method of claim 4, further comprising recording a magnification level of the microscope and transferring the magnification level to the processing apparatus, wherein the processing apparatuses indexes the magnification level with respect to the recording time, the magnified pathology images, and the position of the microscope stage.

6. The method of claim 1, further comprising forming a database with the magnified pathology images and the voice annotations.

7. The method of claim 6, further comprising hosting the database on a remote sever, wherein the remote server is distinct from the processing apparatus, and wherein the processing apparatus is electrically coupled to a network to transfer the magnified pathology images and the voice annotations to the remote server.

8. The method of claim 1, further comprising:
recording geographical information about the pathology sample; and
tracking, with the processor, disease outbreak using the geographical information.

9. The method of claim 1, further comprising: receiving voice commands from the user with the microphone; and executing the commands with the processing apparatus, wherein the commands include at least one of: turning on the microscope, turning on a light source coupled to the microscope, changing a type of light emitted from the light source, or starting recording of the magnified pathology images and the voice annotations.

10. The method of claim 1, further comprising identifying, with the processing apparatus, that the generated image data for the un-imaged holes is not actual image data.

11. The method of claim 10, wherein identifying includes at least one of outlining the generated image data, changing the color of the generated image data, changing the transparency of the generated image data, or labeling the generated image data, when the generated image data is shown on a display.

12. The method of claim 1, further comprising the user directly annotating a region of interest in the magnified pathology images.

13. The method of claim 1, wherein the processing apparatus further performs operations including adjusting a polarization of light from the microscope.

14. A system for pathology data capture, comprising:
a microscope including multiple magnification settings;
a digital camera optically coupled to the microscope to continuously capture magnified pathology images produced by the microscope and output a video including the magnified pathology images;
a microphone coupled to receive voice annotations of a user;
a processing apparatus electrically coupled to the digital camera to receive the magnified pathology images and electrically coupled to the microphone to receive the voice annotations, wherein the processing apparatus includes logic that when executed by the processing apparatus causes the processing apparatus to perform operations including:
recording the magnified pathology images and the voice annotations to a storage medium;
indexing the magnified pathology images and the voice annotations with respect to recording time and tagging the voice annotations of the user to one or more regions of interest in the magnified pathology images;
stitching together the magnified pathology images to form a plurality of high-resolution images, wherein the plurality of high-resolution images include un-imaged holes; and
generating image data that is not actual image data for the un-imaged holes using a machine learning algorithm, wherein the un-imaged holes are disposed between individual magnified pathology images used to form the plurality of high-resolution images.

15. The system of claim 14, wherein the microscope has a stage including first mechanical to electrical transducers to track a position of the stage, wherein the position of the stage is sent from the first mechanical to electrical transducers to the processing apparatus, and wherein the processing apparatus further includes logic that when executed by the processing apparatus causes the processing apparatus to perform operations including:
indexing the position of the stage with respect to the recording time and the magnified pathology images.

16. The system of claim 15, wherein the microscope further comprises second mechanical to electrical transducers to measure the magnification setting of the microscope, and wherein the magnification setting is sent from the second mechanical to electrical transducers to the processing apparatus, wherein the processing apparatus further includes logic that when executed by the processing apparatus causes the processing apparatus to perform operations including:
indexing the magnification setting with respect to the recording time and the position of the stage.

17. The system of claim 14, wherein the processing apparatus further includes logic that when executed by the processing apparatus causes the processing apparatus to perform operations including:
converting the voice annotations to text, wherein the text is indexed with respect to the recording time and the magnified pathology images.

18. The system of claim 14, wherein the processing apparatus further includes logic that when executed by the processing apparatus causes the processing apparatus to perform operations including:
tracking a gaze of the user to determine the one or more regions of interest, and wherein the one or more regions of interest are indexed with respect to recording time, the magnification setting, and magnified pathology images.

19. The system of claim 14, wherein the magnified pathology images and the voice annotations form a database.

20. The system of claim 19, wherein the processing apparatus is electrically coupled to a network and the database is hosted on remote servers.

* * * * *